US009056053B2

(12) United States Patent
Maitra et al.

(10) Patent No.: US 9,056,053 B2
(45) Date of Patent: Jun. 16, 2015

(54) NANOPARTICLE COMPOSITIONS PROVIDING ENHANCED COLOR FOR COSMETIC FORMULATIONS

(75) Inventors: Prithwiraj Maitra, Randolph, NJ (US); Steven Carlo, Monroe, NY (US); Rahul A. Ranade, Hillburn, NY (US)

(73) Assignee: Avon Products, Inc, New York, NY (US)

( * ) Notice: Subject to any disclaimer, the term of this patent is extended or adjusted under 35 U.S.C. 154(b) by 548 days.

(21) Appl. No.: 11/970,882

(22) Filed: Jan. 8, 2008

(65) Prior Publication Data
US 2009/0175915 A1   Jul. 9, 2009

(51) Int. Cl.
| A61Q 1/12 | (2006.01) |
| A61K 8/25 | (2006.01) |
| A61K 8/19 | (2006.01) |
| B82Y 5/00 | (2011.01) |
| A61Q 1/10 | (2006.01) |
| A61K 8/89 | (2006.01) |
| A61K 8/02 | (2006.01) |
| A61K 8/26 | (2006.01) |
| A61K 8/27 | (2006.01) |
| A61K 8/28 | (2006.01) |
| A61K 8/29 | (2006.01) |
| A61K 8/73 | (2006.01) |
| A61K 8/81 | (2006.01) |
| A61K 8/88 | (2006.01) |
| A61Q 1/02 | (2006.01) |
| A61Q 17/04 | (2006.01) |
| A61Q 19/08 | (2006.01) |

(52) U.S. Cl.
CPC ... *A61K 8/25* (2013.01); *A61K 8/19* (2013.01); *A61K 2800/43* (2013.01); *B82Y 5/00* (2013.01); *A61Q 1/10* (2013.01); *A61K 8/89* (2013.01); *A61K 8/0241* (2013.01); *A61K 2800/412* (2013.01); *A61K 8/26* (2013.01); *A61K 8/27* (2013.01); *A61K 8/28* (2013.01); *A61K 8/29* (2013.01); *A61Q 1/02* (2013.01); *A61K 8/731* (2013.01); *A61Q 17/04* (2013.01); *A61K 8/8111* (2013.01); *A61K 8/8117* (2013.01); *A61K 8/8123* (2013.01); *A61K 8/8152* (2013.01); *A61Q 19/08* (2013.01); *A61K 8/88* (2013.01)

(58) Field of Classification Search
USPC ............................................. 424/401, 70.12
See application file for complete search history.

(56) References Cited

U.S. PATENT DOCUMENTS

| 5,356,617 | A  | * | 10/1994 | Schlossman ..................... 424/63 |
| 5,885,921 | A  | * | 3/1999  | Krupey ......................... 502/233 |
| 5,945,095 | A  |   | 8/1999  | Mougin et al. |
| 6,001,373 | A  |   | 12/1999 | Igo-Kemenes et al. |
| 6,375,941 | B1 |   | 4/2002  | Piot et al. |
| 7,351,405 | B2 |   | 4/2008  | De La Poterie |
| 7,993,632 | B2 |   | 8/2011  | Jager-Lezer et al. |
| 2002/0187116 | A1 |   | 12/2002 | De La Poterie |
| 2004/0191200 | A1 |   | 9/2004  | Lezer et al. |
| 2005/0058678 | A1 |   | 3/2005  | Ricard et al. |
| 2005/0128582 | A1 |   | 6/2005  | Gibilini |
| 2005/0169949 | A1 | * | 8/2005  | De La Poterie et al. ...... 424/401 |
| 2006/0013792 | A1 |   | 1/2006  | Fontaine et al. |
| 2006/0013793 | A1 |   | 1/2006  | Themens |
| 2006/0257336 | A1 |   | 11/2006 | Ferrari et al. |
| 2007/0071700 | A1 |   | 3/2007  | Abhimanyu Patil et al. |
| 2010/0266647 | A1 |   | 10/2010 | Dingley et al. |
| 2010/0266648 | A1 |   | 10/2010 | Ranade et al. |

FOREIGN PATENT DOCUMENTS

| FR |   2818898 A1 | * | 7/2002 |
| JP |   H08-157326 |   | 6/1996 |
| JP |   09263518 A2 |   | 10/1997 |
| JP |   2001-187715 A2 |   | 7/2001 |
| JP |   2003113043 A |   | 4/2003 |
| JP |   2004-168662 A2 |   | 6/2004 |
| JP |   2004-189687 A2 |   | 7/2004 |
| JP |   2004238363 A |   | 8/2004 |
| JP |   2005126438 A |   | 5/2005 |
| JP |   2006069933 A |   | 3/2006 |
| JP |   2006273806 A | * | 10/2006 |
| JP |   2007-119410 A2 |   | 5/2007 |

OTHER PUBLICATIONS

Hiroe, K. et al., "Cosmetic for eyelashes", JP 2006-273806PTO 10-0960.*
Hiroe, K. et al. "Cosmetic for Eyelashes", Oct. 12, 2006, JP 2006373806, (English translation), PTO 19-0960.*
Collin, N. et al., "Use of carbon black as curving agent in make-up for coating keratin fibers, useful particularly in mascara, comprises a film-forming polymer", Jul. 5, 2002, Derwent Acc. No. 2008-002410, English Abstract of FR 2818898 A1.*
Flick, E., "Plastics Additives: An Industrial Guide", 1993, (2nd ed.) Noyes Publications, pp. 98 and 149.*
de la Poterie, FR2818900 (Jan. 4, 2001), machine translation.*
Stavenga, et al., Light on the moth-eye corneal nipple array of butterflies, Proc. R. Soc. B, 2005, p. 661-667, vol. 273.
Vukusic, et al., Photonic structures in biology, Nature 2003, p. 852-856, vol. 424.
U.S. Appl. No. 14/040,800, filed Sep. 30, 2013, Maitra et al.
Fragrance Journal, "Technique for Producing Eye Liner, Mascara, Eyebrow Pencil, and Eye Shadow," (1992), vol. 2, pp. 81-87.
Cosmetics manufacturing science, In fact the technology, the company of Fragrance Journal year 2001, Aug. 25th, vol. 1, pp. 221-225.

* cited by examiner

*Primary Examiner* — Gina Justice
(74) *Attorney, Agent, or Firm* — David M. Joyal; Joan M. McGillycuddy (57) ABSTRACT

The present invention relates to cosmetic, dermatological, and pharmaceutical compositions that deliver, in an acceptable vehicle or carrier comprising a film former or wax and an effective amount of nanoparticles and one or more pigments and methods for improving the appearance of a biological surface by altering the optical properties of the biological surface. The compositions of the invention enhance color and may be topically applied to the biological surface in an amount effective in improving the aesthetic and natural appearance of the biological surface.

8 Claims, 7 Drawing Sheets

FIG. 1

Figure 2:
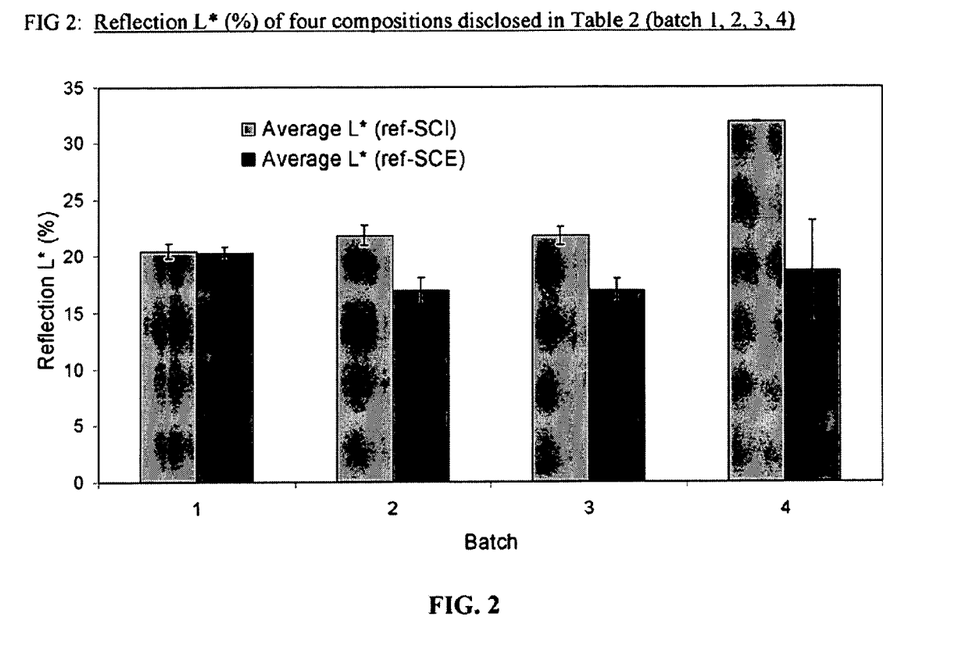

FIG 2: Reflection L* (%) of four compositions disclosed in Table 2 (batch 1, 2, 3, 4)

FIG. 2

FIG. 3

Figure 4:
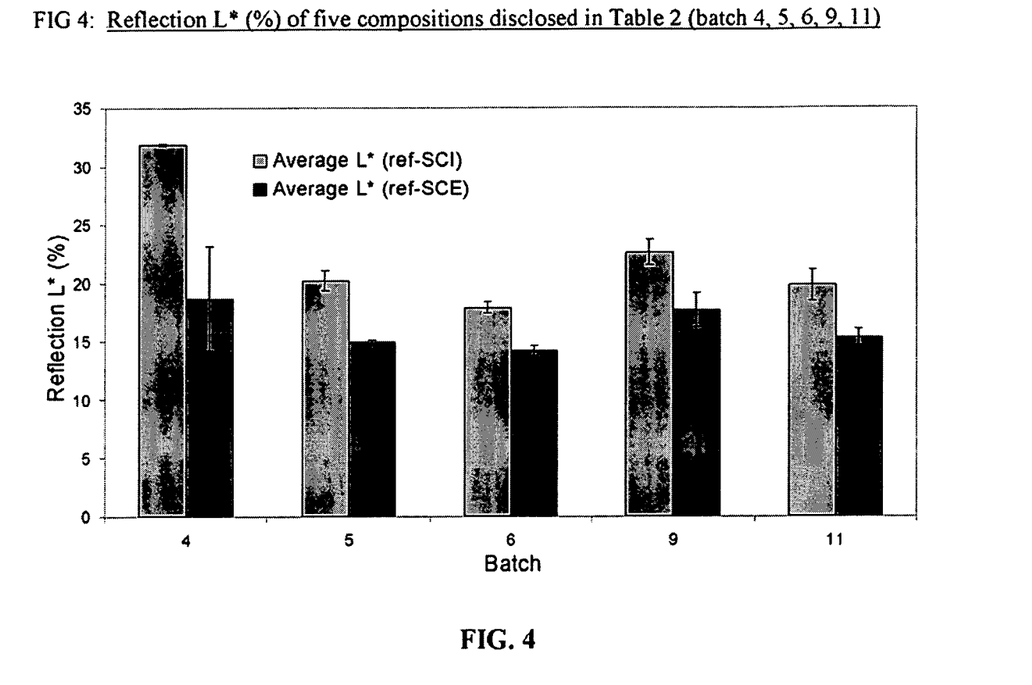

FIG 4: Reflection L* (%) of five compositions disclosed in Table 2 (batch 4, 5, 6, 9, 11)

FIG. 4

Figure 5:
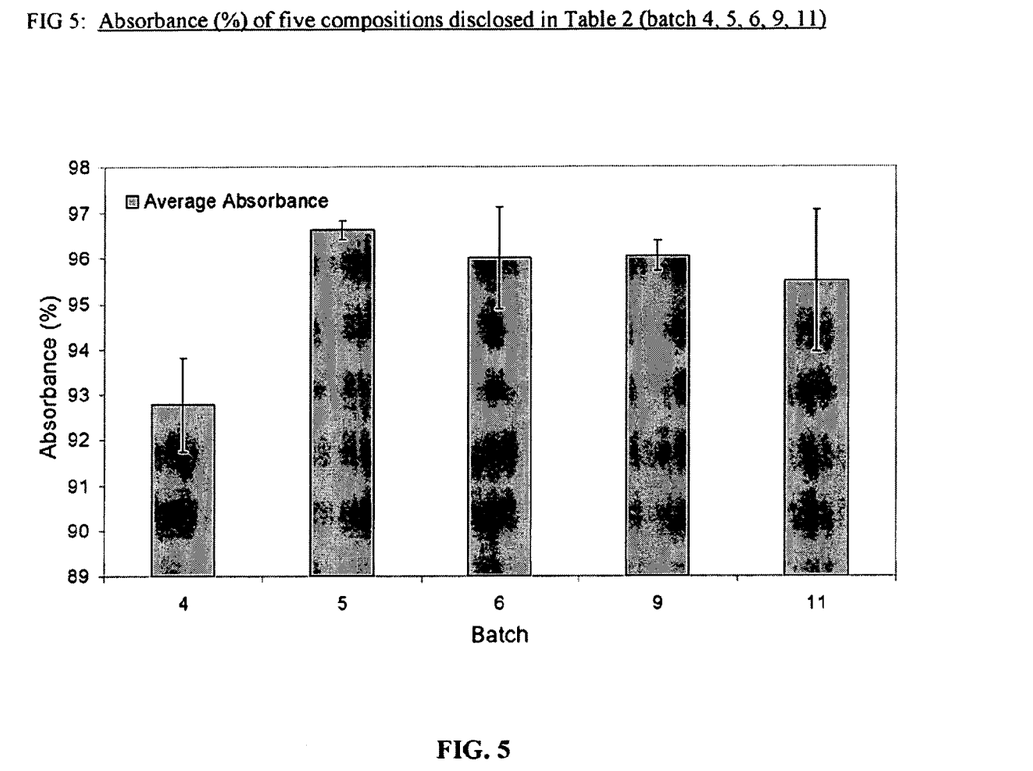

FIG 5: Absorbance (%) of five compositions disclosed in Table 2 (batch 4, 5, 6, 9, 11)

FIG. 5

Figure 6A:
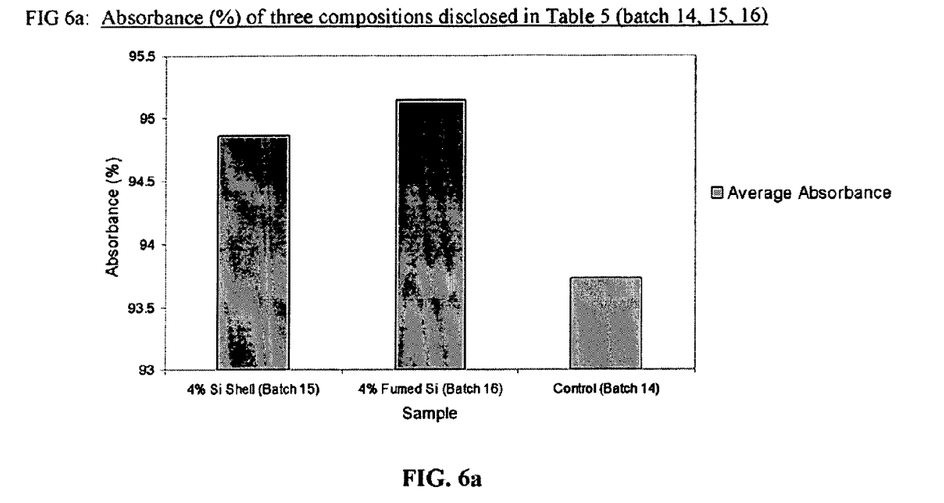

FIG 6a: Absorbance (%) of three compositions disclosed in Table 5 (batch 14, 15, 16)

FIG. 6a

Figure 6B:
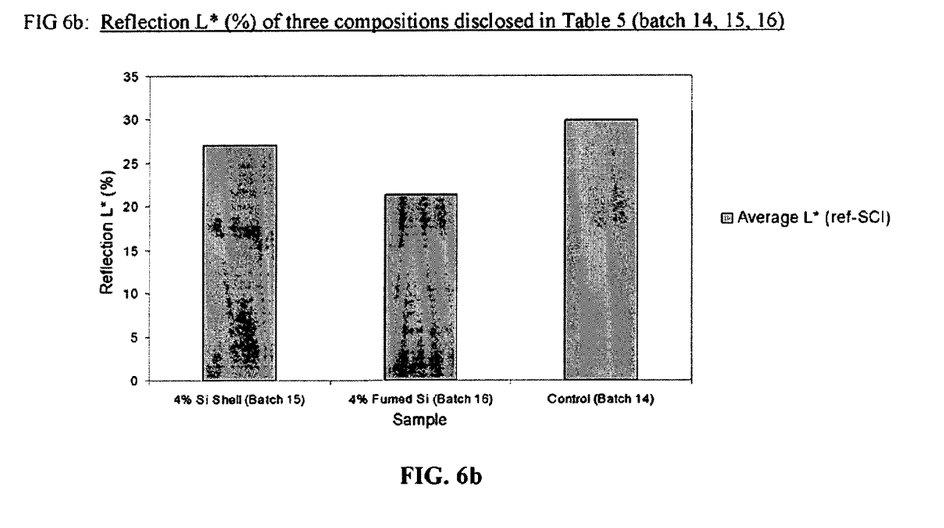

FIG 6b: Reflection L* (%) of three compositions disclosed in Table 5 (batch 14, 15, 16)

FIG. 6b

Figure 7A:
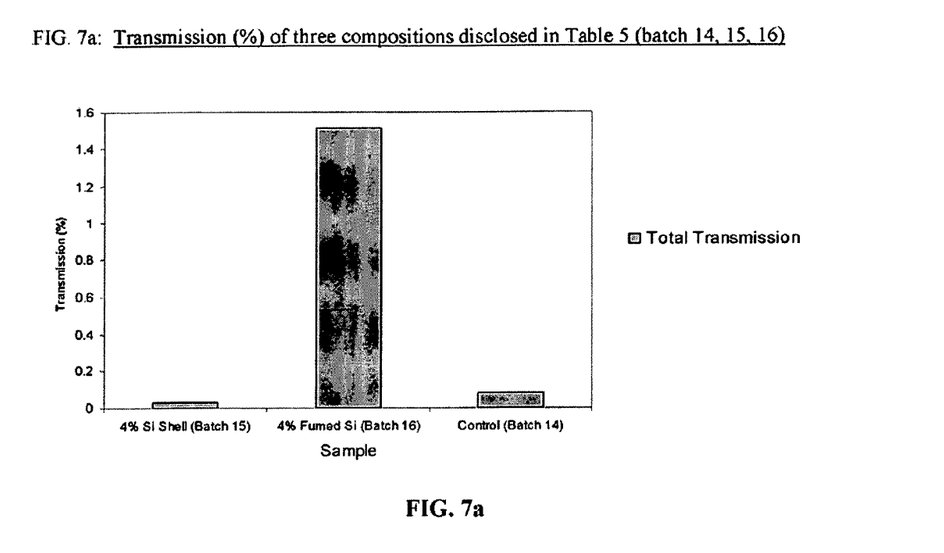

FIG. 7a: Transmission (%) of three compositions disclosed in Table 5 (batch 14, 15, 16)

FIG. 7a

Figure 7B:
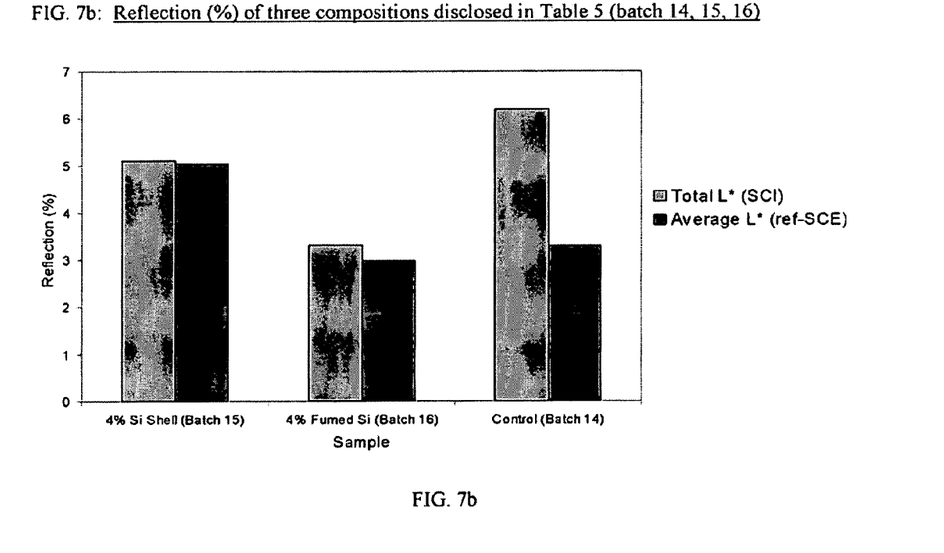

FIG. 7b: Reflection (%) of three compositions disclosed in Table 5 (batch 14, 15, 16)

FIG. 7b

NANOPARTICLE COMPOSITIONS PROVIDING ENHANCED COLOR FOR COSMETIC FORMULATIONS

FIELD OF THE INVENTION

The present invention generally relates to cosmetic, dermatological, and pharmaceutical compositions and their use. More particularly the present invention relates to cosmetic compositions and their use in improving the appearance of biological surfaces.

BACKGROUND OF THE INVENTION

Modern skin care formulations must meet high standards of efficacy, skin compatibility and aesthetic appeal. Consumers are interested in mitigating or delaying the dermatological signs of chronologically-aged, hormonally-aged or photo-aged skin, such as fine lines, wrinkles, drying, and sagging skin, and other conditions due to a progressive degradation of the skin matrix. Consumers are interested in improving the appearance of, for example, skin, lips, nails, and hair by imparting to these biological surfaces a certain color, which would ideally produce an appearance of a uniform, lively, smooth and even surface, with no apparent imperfections. Therefore, there is a need for cosmetics that assist in creating a flawless, long lasting, lively coloring to improve the appearance of the biological surfaces.

Presently, make-up compositions that are applied to biological surfaces to impart a certain color such as foundations, face powders, eyeshadows, lipsticks, concealers, blushers, mascaras, eyeliners, lip pencils, eye pencils, or nail varnishes have difficulty achieving a perfect, flawless lively color because cosmetic ingredients such as coloring agents, which provide the desired color and coverage, generally have many limitations.

The coloring agents employed in such make-up compositions can be lakes, inorganic or organic pigments and/or pearlescent pigments, and alternatively dyes. Inorganic pigments, and in particular inorganic oxides, have the advantage of being relatively stable, but have the drawback of imparting rather dull, pale colors to the material being colored. Organic lakes have the advantage of imparting lively colors to the compositions, but are relatively unstable with respect to light, temperature or pH. Some of these coloring agents also have the drawback of leaving unsightly marks on the skin or the nails after application. Pearlescent pigments allow varied, but not intense, colors to be obtained with iridescent effects. Moreover, certain coloring agents have the drawback of generating free radicals in make-up formulations, which modify the color of the applied make-up and the stability of the compositions. Free radicals, when present on the skin promote ageing of the skin such as the appearance of wrinkles, fine lines and yellowing of the skin.

Therefore, there remains a need for cosmetic formulations and preparations that provide the increased color chroma of organic lakes while having the stability of inorganic pigments.

The compound eyes of insects are composed of ommatidia. The ommatidia have smooth surfaces, but some, such as those of moths and butterflies, are covered with tiny, slightly tapered protuberances. These structures are approximately 200 nanometers in both height and diameter at their base, and are arrayed across the surface of the ommatidia in a regular hexagonal pattern. These structures were first observed in nocturnal moths by W. H. Miller and colleagues in 1962 (Bernhard C. G. and Miller W. H. "A corneal nipple pattern in insect compound eyes," *Acia Physiol. Scand.* 1962;56:385-386). Such structures are shown and described in Vukusic, et al., *Nature* 2003, 424:852-856, for example, FIG. 7.

Because the species that possess these structures tend to be active at night or in the dark, it is important that they absorb as much of the available light as possible. The function of such protuberances seems to be to reduce reflection of light from the surface of the ommatidia and thereby increase light's absorption by the receptor cells underneath. Like much of the exoskeleton of insects, the surface of each ommatidium is made of chitin, which has a refractive index (1.55) higher than that of air (1.00).

The protuberances work by providing a gradual transition in refractive index from air to ommatidium. Each individual photon that is incident on the ommatidia first encounters the thinner tops of the protuberances, making the effective refractive index only slightly higher than the refractive index of air. As the protuberance widens closer to the bottom, the refractive index of the surface approaches that of pure chitin. Because the size and periodicity of the protuberances are smaller than those of the optical wavelengths absorbed (<~500 nm), each individual photon encounters this gradual transition, and reflection from the surface is minimized. This is known as the "moth-eye principle" or the "moth-eye effect".

The moth-eye structure is well suited for many antireflective tasks. In the present application, the inventive cosmetic formulations permit increased light absorption and provide increased color chroma while being relatively stable.

SUMMARY OF THE INVENTION

It is an object of the present invention to provide a composition that delivers in an acceptable carrier comprising a film former and/or wax, an effective amount of a nanoparticle material and one or more pigments sufficient to alter the appearance of a biological surface, where the composition controls light transmission, absorption and scattering. It is a further object to provide cosmetic formulations that provide high color chroma. When the inventive formulations are black, it is a further object permit increased light transmission and absorption and reduced light reflection.

It is another object of the present invention to provide a method of making a composition of nanoparticle material and pigment in acceptable vehicle or carrier.

A further object of the invention is to provide a composition comprising an effective amount of nanoparticles to produce the optical effects observed in the moth eye along with one or more pigments in a carrier which further produce unique optical effects on skin. In yet another object, a method of improving the aesthetic or natural appearance of a biological surface by applying to the biological surface a composition comprising an effective amount of nanoparticles to produce optical effects observed in the moth eye and one or more pigments in a carrier in an amount effective to improve the aesthetic or natural appearance of the biological surface. The composition is applied such that the appearance of dermatological signs of damaged or chronologically-aged, hormonally-aged, or photo-aged skin, such as fine lines, wrinkles, and sagging skin, surface imperfections, and discoloration is diminished.

It is another object of the present invention to provide a method of beautifying and decorating a biological surface by applying to the biological surface a composition comprising a carrier having a film former and/or wax with an effective amount of nanoparticles and one or more pigments to produce the optical effects observed in the moth eye. The composition is applied to a biological surface to add color, hide surface flaws, act as a photoprotectant, and make the surface appear smoother.

These and other objects and advantages of the present invention, and equivalents thereof, are achieved by compositions having an effective amount of nanoparticles along with pigments and combinations thereof, and methods of using such compositions for topical application in order to improve the aesthetic appearance of a biological surface.

BRIEF DESCRIPTION OF THE DRAWING

FIG. 1 shows a schematic representation of the anti-reflective "moth-eye" surface with the size of the moth-eye structure between 180 nm and 240 nm. This sub-visible light wavelength surface relief profile is a low reflectance interface for light. As a result, the moth's eye appears black and may absorb light from any direction.

FIG. 2 shows the reflectance (total reflection (SCI) and scattering reflection (SCE)) of four systems: (1) 6.94% carbon black plus 2.78% hydrophobic silica; (2) 6.94% carbon black plus 2.78% hydrophobic fumed silica; (3) 6.94% carbon black plus 2.78% fumed silica and (4) 7.14% carbon black. The full composition of each system is disclosed in Table 2. The figure shows that the addition of silica of any kind reduces total reflection (SCI—specular component included).

FIG. 3 shows absorbance of the four (4) systems used in FIG. 2. The figure shows that the addition of silica of any kind increases absorption. The reflection and absorption values for each system disclosed in Table 2 are shown in Table 3.

FIG. 4 shows the reflectance (total reflection (SCI) and scattering reflection (SCE)) of five systems: (5) 6.94% carbon black plus 5.00% fumed silica; (6) 6.94% carbon black plus 7.00% fumed silica; (9) 9.00% carbon black plus 2.78% fumed silica; (11) 9.00% carbon black plus 5.00% fumed silica; and (4) 7.14% carbon black. (The full composition of each system is disclosed in Table 2). The figure shows that the addition of fumed silica to carbon black causes a decrease in total reflection.

FIG. 5 shows absorbance of the five systems used in FIG. 4. The figure shows that the addition of fumed silica to carbon black increases absorption.

FIG. 6*a* shows the absorbance and FIG. 6*b* shows the luminescence (L*) data for three (3) systems: 4.00% carbon black control with no nanoparticles, 4.00% carbon black with 4% silica shell nanoparticles, and 4.00% carbon black with 4.00% fumed silica nanoparticles. The figures shows that the addition of either 4.00% fumed silica nanoparticles or 4.00% silica shell nanoparticles results in increased absorbance and reduced luminescence resulting in enhanced contrast (darker) in comparison to the carbon black control (no nanoparticles). The full composition of each system is disclosed in Table 5.

FIG. 7*a* shows the total transmission and FIG. 7*b* shows the total reflectance and scattered reflectance data for three (3) systems: 4.00% carbon black control with no nanoparticles, 4.00% carbon black with 4.00% silica shell nanoparticles, and 4.00% carbon black with 4.00% fumed silica nanoparticles,. The figures show that addition of 4.00% fumed silica nanoparticles results in increased transmission, reduced total reflectance and reduced scattered reflectance. The full composition of each system is disclosed in Table 5. The reflection and absorption values for each system disclosed in Table 5 are shown in Table 6.

DETAILED DESCRIPTION OF THE INVENTION

In accordance with the foregoing objectives and others detailed herein, the invention provides compositions comprising an effective amount of nanoparticles in combination with a pigment in an acceptable vehicle having a film former and/or wax to create optical effects observed in the moth eye which improve the aesthetic appearance of biological surfaces. The compositions, for example, improve the appearance of biological surfaces damaged by the chronological aging process, the environment, or natural imperfections. The compositions also serve to beautify and decorate the biological surfaces. When applied to a surface, for example, a biological surface, the compositions enhance the appearance of the surface by enhancing absorbance, enhancing transmittance and reducing reflective properties. Enhancing the aesthetic appearance of the biological surfaces may be achieved by topical application of the inventive compositions to the biological surfaces on a daily basis or when a natural appearance or added color is desired. Biological surfaces include, but are not limited to, keratinous tissues, skin, hair, lips, eyelashes, eyebrows and nails.

The compositions of the invention alter the manner in which light reaches a biological surface so as to provide hiding, opacity, and coverage. The inventive compositions comprise transparent or translucent nanoparticles along with a cosmetic pigment. The nanoparticles in combination with pigment present in a cosmetic composition are suitable for application to biological surfaces.

The term "nanoparticle" as used herein refers to a nanometer-sized particle, having a diameter of between about 1 nanometer and about 999 nanometers; the term "nanoparticles" as used herein refers to nanometer-sized particles, nanoclusters, clusters, particles, small particles, and nanostructured materials.

An effective amount of nanoparticle material in an acceptable carrier depends on factors including the weight ratio of nanoparticles plus pigment to film former and/or wax in the carrier, the surface area of each nanoparticle, the physical properties of the nanoparticles and the weight ratio of nanoparticles to the pigment. The pigment, carrier and nanoparticle material may each have a different refractive index so as to control light diffusion properties. The refractive index of the pigment is greater than the nanoparticle material to obtain optimal lateral light diffusion. The size of each nanoparticle is preferably less than the wavelength of visible light to enhance light absorption and reduce reflectance.

Pigments suitable in this invention range in particle size from about 100 nanometers to about 10 microns. More preferably, pigment particle sizes range from about 100 nanometers to about 2 microns. Preferred inorganic pigments for use in this invention are those typically used in the personal care or cosmetic industry to provide hiding, coverage and/or color. In one embodiment of the invention, the pigment material is about 0.5 microns; in another embodiment of the invention, pigment material is about 1.0 microns. Reference to the size of a pigment or nanoparticle means the length of the largest straight dimension of the pigment or nanoparticle. By way of example, the size of a spherical pigment is its diameter, and the size of a spherical nanoparticle is its diameter.

The refractive index of the pigments can be from about 1.38 to about 3.52; more preferably about 1.40 to about 3.50; more preferably about 1.42 to about 3.40; more preferably about 1.60 to about 3.40. Pigments having refractive indices of about 1.38 to about 3.52 include, but are not limited to, titanium dioxide (rutile or anatase), zinc oxide and iron oxide. The refractive indices of various materials may be evaluated using a refractometer. Details with respect to the principles of refraction can be found in Optics by Eugene Hecht (Fourth Edition), 2002. Details with respect to refractive indices of materials can be found in the CRC Handbook of Chemistry and Physics, 86th Edition, 2005-2006, which is herein incorporated by reference in its entirety.

In one embodiment, the composition is comprised of a combination of pigments of different refractive indices. In another embodiment of the invention, the composition is comprised of a single pigment.

Suitable inorganic pigments include, but are not limited to, titanium dioxide, zirconium oxide and cerium oxide, as well as zinc oxide, iron oxide, chromium oxide and ferric blue. Suitable organic pigments include, but are not limited to, barium, strontium, calcium, and aluminum lakes and carbon black. Any pigment material of the inventive composition producing the desired effects may be used, non-limiting examples of which include a metal oxide, for example, titanium dioxide, iron oxide, and aluminum oxide. For typical pigments used in cosmetic industry, refer to the Cosmetic Ingredient Dictionary (INCI) and Handbook, 10th Edition (2004), published by the Cosmetic, Toiletry, and Fragrance Association (CTFA).

In one embodiment, the composition comprises titanium dioxide. In another embodiment, the composition comprises iron oxide In another embodiment, the composition comprises carbon black.

Organic and inorganic pigments suitable for use in this invention may be substantially solid or porous. In one embodiment, the outer surface of the pigment is substantially solid and of uniform contour.

Nanoparticles suitable to create the desired optical effects observed in the moth eye of this invention range in size from about 1 nm to about 900 nm; more preferably from about 7 nm to about 700 nm; more preferably from about 10 nm to about 500 nm. Mean particle sizes of nanoparticles of this invention range in size from about 10 nm to about 700 nm; more preferably from about 20 nm to about 500 nm; more preferably from about 30 nm to about 500 nm. In various embodiments of the invention, the mean particle size of the nanoparticles may be about 10 nm, about 20 nm, about 50 nm, about 75 nm, about 100 nm, about 125 nm, about 150 nm, about 175 nm, about 200 nm, about 225 nm, about 250 nm, about 275 nm, about 300 nm, about 325 nm, about 350 nm, about 375 nm, about 400 nm, about 425 nm, about 450 nm, about 475 nm, or about 500 nm. Preferably, the nanoparticles have a diameter below the wavelength of light they are interacting with, thereby producing the desired effects.

In one embodiment of the invention, the nanoparticles are smaller than the size of the pigment. In another embodiment of the invention, the nanoparticles are about the same size as the pigment. In yet another embodiment of the invention, the nanoparticles are larger than the size of the pigment.

Nanoparticles suitable for this invention include, but are not limited to, nanoparticles made of fumed silica, metal oxides such as aluminum oxide, fumed alumina, zinc oxide, titanium dioxide or zirconium oxide, or polymeric nanoparticles such as poly(methyl methacrylate) (PMMA), nylon, polyethylene (PE), polystyrene (PS), polytetrafluoroethylene, or cellulosics. The refractive index of the nanoparticles can be from about 1.30 to about 3.50. In one embodiment of the invention, the nanoparticle is fumed silica having a refractive index of about 1.46. In one embodiment, the composition is comprised of a combination of nanoparticles of different refractive indices.

The nanoparticles in the composition are capable of enhancing the absorption and/or altering the scattering behavior of visible light. The difference between the refractive indices of the cosmetic pigment and nanoparticle material may range from about 0.01 to about 2.0. In one embodiment of the invention, the difference between the refractive indices of the cosmetic pigment and nanoparticle material is about 2.0. In another embodiment of the invention, the difference between the refractive indices of the cosmetic pigment and nanoparticle material is about 1.0. In another embodiment of the invention, the difference between the refractive indices of the cosmetic pigment and nanoparticle material is about 0.7. In another embodiment of the invention, the difference between the refractive indices of the cosmetic pigment and nanoparticle material is about 0.5.

Compositions comprising a pigment having a high refractive index along with nanoparticles having a low refractive index permit a change in the direction of light at the surface interface to occur thus enhancing light absorption and diffusion, and reducing light reflection and scattering which results in high coverage along with reduced glossiness, enhanced natural or added color contrast and a blurring effect. In one embodiment of the invention, the refractive index of the cosmetic pigment is about 2.02; in another embodiment of the invention, the refractive index of the pigment is about 2.19.

Weight ratio of the nanoparticles to the pigment particles in the inventive compositions may range from about 10.0:1.0 to about 1.0:10.0. Weight ratios determine the relative percentage of nanoparticles to the pigment particles, thereby affecting the refractive index of the composition. In one embodiment of the invention, the composition has a weight ratio of nanoparticles to pigment particles of about 4.0:1.0; in another embodiment of the invention, the composition has a weight ration of nanoparticles to pigment particles of about 1.0:4.0; in another embodiment of the invention, the composition has a weight ratio of nanoparticles to pigment particles of about 1.0:1.0, in another embodiment of the invention, the composition has a weight ratio of nanoparticles to pigment particles of about 1.0:1.4; in yet another embodiment of the invention, the composition has a weight ratio of nanoparticles to pigment particles of about 1.0:1.8; in another embodiment of the invention, the composition has a weight ratio of nanoparticles to pigment particles of about 1.0:3.0. In a preferred embodiment of the invention the composition has a weight ratio of nanoparticles to pigment particles of about 1.0:1.4.

The weight ratio of nanoparticles plus pigment particles to film former and/or wax present in the carrier may range from about 100.0:1.0 to 1.0:5.0, more preferably from about 100.0:1.0 to about 1.0:1.75, more preferably from about 100.0:1.0 to about 1.05:1.0, more preferably from about 20.0:1.0 to about 1.05:1.0, more preferably from about 10.0:1.0 to about 1.05:1.0, more preferably from about 2.0:1.0 to about 1.05:1.0. The weight ratio of nanoparticles plus pigment particles to film former and/or wax present in the carrier determines the relative percentage of nanoparticles within the composition that are responsible for creating the optical effects observed in the moth eye, that is, increasing the light absorbance.

In the L* a* b* color space (also known as CIELAB), L* indicates lightness and a* and b* are the color directions. L* is measured from 0 (black) to 100 (white). The values of a* and b* are plotted in the xy coordinate plane such that +a is red, −a is green, +b is yellow, and −b is blue. The origin (center) of the a* b* plane is achromatic, and an increase in (+/−) a* or (+/−) b* results in an increase of the color chroma. When the inventive formulations have colored pigments, the formulations have increased color chroma, that is, increased (+/−) a* or (+/−) b* values. When the inventive formulations are black, the formulations have increased light absorption and decreased light reflection, that is, a decreased L* value (i.e., a more intense black). Table 1 shows examples of mascara formulations and their respective L* values. The mascara formula with the hydrophobic amorphous filmed silica shows the lowest L*.

TABLE 1

Examples of mascara formulations demonstrating their respective L* values

|  | 1 | 2 | 3 |
|---|---|---|---|
| Kobo Black iron oxide pigment | 4.00 | 4.00 | 4.00 |
| Aeroxide LE 3 (deGussa) | 0 | 4.00 | 0 |
| Cadre Hydrophobic Amorphous Fumed Silica # 79684 | 4.00 | 0 | 0 |
| KP-550 (Shin Etsu) | 5.60 | 5.60 | 5.60 |
| Versagel MD 1600 (Panerco) | 56.00 | 56.00 | 56.00 |
| Isododecane | 30.40 | 30.40 | 30.40 |
| (TOTAL) | 100 | 100 | 100 |
| L* Value | 15.40 | 19.00 | 25.00 |

In one embodiment of the invention, the weight ratio of nanoparticles plus pigment particles to film former and/or wax present in the carrier is about 1.0:1.0; in another embodiment of the invention, the weight ratio of nanoparticles plus pigment particles to film former and/or wax present in the carrier is about 1.4:1.0. In one embodiment of the invention, the weight ratio of nanoparticles plus pigment particles to film former and/or wax present in the carrier is about 1.7:1.0; in another embodiment of the invention, the weight ratio of nanoparticles plus pigment particles to film former and/or wax present in the carrier is about 2.0:1.0

Suitable film formers for use in the inventive compositions include, but are not limited to, sulfopolyester resins, polyvinylacetate, polyvinyl alcohol polymers, acrylic resins, silicone acrylate polymers (such as those available from Shin Etsu), polyvinylpyrrolidones, high molecular weight silicones, organosiloxanes, polyurethanes, hydrophobic acrylate copolymers, as well as others known in the art (for example those listed in WO 03/105790, incorporated herein). The film former is preferably present from about 0.01 weight % to about 20 weight % of the total weight of the composition. In one embodiment, the film former is a polymer. In one embodiment, the film former is silicone acrylate copolymer.

In one embodiment of the invention, the composition includes one or more waxes, gums, or mixtures thereof. Suitable waxes include hydrocarbon-based waxes, fluoro waxes and/or silicone waxes and can be of plant, mineral, animal and/or synthetic origin. In particular, the waxes have a melting point of greater than 25° C., preferably greater than 45° C. The compositions of the present invention may contain from about 0.1 weight % to about 20 weight % waxes, based upon the total weight of the composition. The gums are generally high molecular weight polydimethylsiloxanes (PDMSs), cellulose gums or polysaccharides, and the semi-solid materials are generally hydrocarbon-based compounds, such as, but not limited to, lanolins and derivatives thereof, or alternatively PDMSs. The compositions of the present invention may contain from about 0.1 weight % to about 20 weight % gums, based upon the total weight of the composition, typically from about 0.5 weight % to about 10 weight %.

The surface area of the nanoparticles of the inventive compositions may range from about 20 $m^2/g$ to about 700 $m^2/g$; more preferably about 50 $m^2/g$ to about 500 $m^2/g$; more preferably about 70 $m^2/g$ to about 400 $m^2/g$. Surface area of the nanoparticles governs the multiple scattering of light in the composition.

The compositions of the present invention can be prepared by combining a specific amount of pigment, nanoparticles, and a carrier with already premixed solvents, one or more film-formers and/or waxes and other desired ingredients. The components are to be mixed with very high shear blade mixers for a sufficient period of time to make a homogeneous mixture. It will be recognized that the time and the sequence of adding compounds may vary depending on the components of the desired composition.

The compositions of the present invention provide increased color chroma of the pigment used, regardless of the type of pigment employed. Accordingly, the inventive compositions can provide color chroma from organic pigments that is similar to color chroma of organic lakes. Such compositions would then have the benefit of high color chroma usually associated with organic pigments but with the stability associated with inorganic pigments.

In situations where the inventive compositions lack a pigment it is believed that the compositions will increase light transmission and provide increased color chroma of a biological surface to which the compositions are applied. Such inventive compositions are useful for enhancing the natural color of a biological surface. In situations where the inventive composition lacks a pigment, the weight ratio of nanoparticles to film former and/or wax present in the carrier may range from about 100.0:1.0 to 1.0:5.0, more preferably from about 20.0:1.0 to about 1.05:1.0, more preferably from about 10.0:1.0 to about 1.05:1.0, more preferably from about 2.0:1.0 to about 1.05:1.0.

Figure 1:
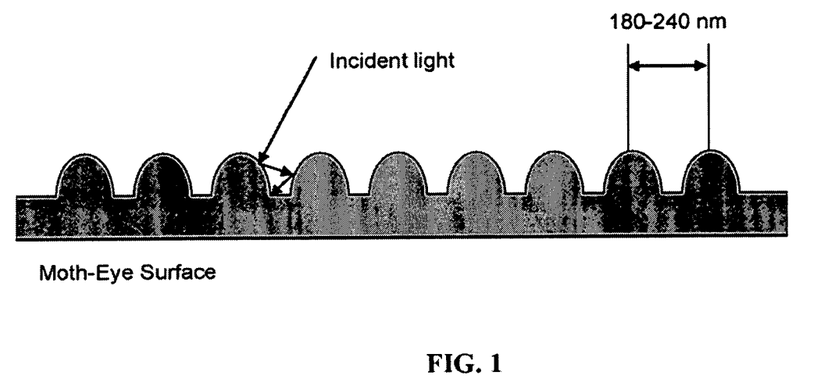

In the moth's eye, the light enters the crevices between conical protrusions that are less than 500 nm in diameter (FIG. 1). The inventive compositions may contain nanoparticles having a low refractive index; the inventive compositions have nanoparticles that are preferably of sub-visible light wavelength size to create the optical effects observed in the moth eye.

Without wishing to be bound by any particular theory or mechanism, it is believed that when a composition of the invention is applied as a layer to a biological surface, the nanoparticles aggregate on the layer's outer surface (that is, the surface opposite to the surface adjacent to the biological surface). If such aggregation occurs, then the layer's outer surface would have a morphology similar to that of a moth's eye. The nanoparticle aggregation on the layer's outer surface would be dependent on the weight ratio of nanoparticles plus pigment to film former in the carrier. At specific weight ratios disclosed herein, the nanoparticles of the inventive compositions are exposed to incident light. It is believed that when incident light strikes the nanoparticles, light is absorbed and scattered which decreases light reflectance.

Design and choice of nanoparticles may increase the angle of incidence to greater than the critical angle for total internal reflection, thus enhancing the light diffusion along the interface of nanoparticles and pigment. By using nanoparticles having a low reflective index, one can obtain high coverage along with enhanced color. A composition comprising nanoparticles having a low refractive index along with a pigment having a high index of refraction enables the composition to produce a more natural appearance when applied to skin by enhancing transmittance.

The advantages of the inventive composition include, but are not limited to, the simplicity of providing enhanced color and while employing cosmetically acceptable pigments and carriers.

If the nanoparticles in the inventive compositions are small, for example, about 100 nanometers or less, then films and coatings may be produced that, in addition to creating optical effects observed in the moth eye, may also provide ultraviolet (UV) protection. Another advantage of the nanoparticles is that they may absorb oil, sebum, and moisture. These properties provide additional benefits in cosmetic and dermatological formulations or compositions, and enhance the aesthetic and natural appearance of biological surfaces.

Compositions of the present invention have optical properties which enhance the aesthetic and natural appearance of a biological surface by enhancing the color of the pigments or dyes. When applied to a biological surface, the inventive compositions result in optical blurring and increased light transmittance, light scattering and reduced, thereby reducing the appearance of dermatological signs of chronological-aging, photo-aging, hormonal-aging, and/or actinic-aging; reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; reducing the appearance and/or depth of lines and/or wrinkles; improving the appearance of suborbital lines and/or periorbital lines; reducing the appearance of crow's feet; improving the appearance of rejuvenating and/or revitalizing skin, decreasing the appearance of aging skin; reducing the appearance of skin fragility; reducing the appearance of a loss of glycosaminoglycans and/or collagen; reducing the appearance of estrogen imbalance; reducing the appearance of skin atrophy; reducing the appearance of hyperpigmentation; reducing the appearance of skin discoloration; improving the appearance of skin tone, radiance, clarity and/or tautness, reducing the appearance of sagging skin; improving the appearance of skin firmness, plumpness, suppleness and/or softness; improving the appearance of procollagen and/or collagen production; improving the appearance of skin texture and/or retexturization; improving the appearance of skin barrier repair and/or function; improving the appearance of skin contours; improving the appearance of decreased skin luster and/or brightness; improving the appearance of dermatological signs of fatigue and/or stress; improving the appearance of environmental stress; improving the appearance of cellular aging; improving the appearance of skin dehydration; improving the appearance of elastic and/or resilient skin; improving the appearance of microcirculation; decreasing the appearance of cellulite formation; or any combinations thereof.

Another embodiment of the invention relates to a method of improving the aesthetic or natural appearance of a biological surface comprising applying to the biological surface, including but not limited to, keratinous tissue, skin, hair and nails, the inventive composition having the characteristics and properties described herein, in an amount effective to improve the aesthetic or natural appearance of the biological surface.

The biological surface may be any surface to which cosmetics, personal care products, dermatological, and pharmaceutical compositions are typically applied, including but not limited to skin, lips, hair, nails, and the like. The composition that is applied to skin improves or enhances the aesthetic appearance of skin by camouflaging the natural aging process, discoloration, chronic and cumulative damage to biological surfaces, and imperfections on the surface. The composition that is applied to keratinous surface or a mucous membrane improves or enhances the aesthetic appearance of the surface by enhancing the natural color and color added in the form of the pigment.

Embodiments of the invention relate to the discovery that nanoparticles in a composition that produces optical effects observed in the moth eye can camouflage biological surface flaws and add color with increased chroma to the biological surface. Thus, the optical properties of the inventive compositions enable one to camouflage imperfections of biological surfaces and add colors and shades with increased chroma, thereby improving the aesthetic and natural appearance of biological surfaces. The optical properties of the inventive compositions also allow one to beautify and decorate a biological surface.

One embodiment of the invention relates to methods of applying the claimed composition to an affected area of the skin. The composition is preferably applied topically as desired by the user any number of times during the day, and remains on the affected area of the skin, where the affected area of the skin includes, but is not limited to, the face, neck, legs and thighs, scalp, and overall body. Topical compositions preferably have the aforementioned nanoparticles in combination with pigments which improves the cosmetic and/or aesthetic appearance of skin, particularly of aging and/or inflamed skin.

The inventive compositions are useful in improving the natural and aesthetic appearance of biological surfaces including skin, lips, hair, and nails, when applied, preferably topically as many times as desired by the user to the biological surface. The compositions of the invention may also include, in addition to a carrier or vehicle, non-limiting examples of active ingredients useful in reducing, diminishing, or camouflaging medical and/or cosmetic conditions associated with aging, inflammation, and degeneration of the biological surface. Such conditions, as used herein, commonly include, but are not limited to, dermatological aging (chronological aging, hormonal aging and/or actinic aging), dermatitis, skin and hair fragility, hirsutism, rosacea, skin blemishes, sensitive skin, hyperpigmentation or hypopigmentation, thinning skin, roughness, keratosis, skin atrophy, wrinkles, lines, hyperplasia, fibrosis, and any combinations thereof. The active components of the present invention may also be useful in enhancing the general health, vitality, condition, and aesthetic appearance of the skin.

In accordance with the invention, compositions having the desired properties may be useful in topically applied formulations, anti-oxidants, anti-inflammatories, sunscreens, cosmetics, including makeup, and formulations for reducing dermatological signs of aging, including wrinkles, fine lines, and sagging skin, and the like. Also in accordance with this invention, compositions may be formulated in a variety of product forms. The compositions may be prepared in targeted delivery systems, e.g. creams, lotions, moisturizers, gels, toners, serums, sprays, foams, powders, and the like, particularly for topical application and administration.

The inventive compositions are preferably for topical administration or for targeted delivery without inducing significant irritation. The inventive compositions are suitable for all skin types, such as sensitive, normal, dry, or oily, preferably sensitive to dry skin, as well as mature skin. In particular embodiments, the compositions may be suitable for dry skin. The compositions are applied to the skin for a period of time sufficient to enhance the natural and aesthetic appearance of skin. The compositions may be applied topically once, twice, or more daily to biological surfaces, including but not limited to skin, lips, and hair.

The topical compositions may be formulated into liposomes which may comprise other additives or substances, and/or which may be modified to more specifically reach or remain at a site following administration. The compositions of embodiments of the present invention yield improvements to the aesthetic appearance of skin by camouflaging or improving upon at least one of the previously described conditions, or combinations thereof.

The inventive compositions may be topically applied as described herein according to the routine technique for administering such compositions. The topical cosmetic, dermatological, or pharmaceutical composition preferably is applied once or multiple times daily. The cosmetic composition is preferably applied to the face and neck, but may be applied to any area of skin in need of aesthetic improvement, where the cosmetic composition remains on the affected area of skin, and preferably not removed or rinsed off the skin. Routine and commonly practiced techniques encompass the application of creams, lotions, gels, sera, ointments, makeup, sunscreen compositions, or the like, to the skin. Preferably the cosmetic composition is a topical leave on formulation, where spraying as a form of application is also envisioned.

The inventive compositions are suitable for contact with living mammalian tissue, including human tissue, or synthetic equivalents thereof, with virtually no adverse physiological effect to the user. Compositions embraced by this invention can be provided in any cosmetically and/or dermatologically suitable form, preferably as a lotion or cream, but also in an anhydrous or aqueous base, as well as in a sprayable liquid form. Other suitable cosmetic product forms for the compositions of this invention include but are not limited to, for example, an emulsion, a cream, a balm, a gloss, a lotion, a foam, a mask, a serum, a toner, an ointment, a mousse, a patch, a pomade, a solution, a spray, a wax-based stick, or a towelette. In addition, the compositions contemplated by this invention can include one or more compatible cosmetically acceptable adjuvants commonly used and known by the skilled practitioner, such as fragrances, emollients, humectants, preservatives, vitamins, chelators, thickeners, perilla oil or perilla seed oil (WO 01/66067 to a "Method of Treating a Skin Condition," incorporated herewith) and the like, as well as other botanicals such as aloe, chamomile, and the like, and as further described below.

The nanoparticles in combination with pigment of the present invention may be contained in a cosmetically, dematologically, physiologically, and pharmaceutically acceptable vehicle, medium, diluent or carrier, for use in reducing, ameliorating, or preventing the dermatological signs associated with aging and inflammation of biological surfaces. In an embodiment embracing topical applications, the compositions of this invention comprise a medium (vehicle, diluent or carrier) that is compatible with mammalian biological surfaces, including skin, lips, hair and nails. The compositions can be formulated as an aqueous phase, an oil phase, alcohol, or aqueous/alcohol-based solutions, ointments, creams, lotions, gels, a wax-in-water emulsion, or water-in-oil, oil-in-water, of water-oil-water triple emulsions having the appearance of a cream or gel, microemulsions, or aerosols.

The aqueous phase is a mixture of one or more water soluble or water dispersible ingredient, which can be liquid, semi-solid or solid at room temperature (25° C.). The vehicle comprises or can be in the form of a suspension, dispersion or solution in water or an aqueous-alcoholic vehicle, which may contain a thickener or gellant. A person skilled in the art can select the appropriate cosmetic form, the ingredients contained therein, as well as the method for preparing it, on the basis of the knowledge that the skilled artisan possesses.

In one embodiment, the composition may include an aqueous phase which may contain water or a mixture of water and at least one hydrophilic organic solvent in particular an alcohol, especially a linear or branched lower monoalcohol containing from 2 to 5 carbon atoms, e.g., ethanol or propanol; a polyol, e.g., propylene glycol, sorbitol, glycerol, diglycerol, panthenol, or polyethylene glycol, and mixtures thereof. This aqueous phase may represent from about 0.5 weight % to about 99.99 weight %, based upon the total weight of the composition.

In another embodiment when the composition of the invention is in the form of an emulsion, the composition may also optionally comprise a surfactant, preferably in an amount of from about 0.1 weight % to about 30 weight %, and in particular, from about 1 weight % to about 20 weight %, based upon the total weight of the composition.

In a further embodiment of the invention, the composition may also comprise a thickening polymer such as an amphiphilic polyurethane, a polyacrylic homopolymer or copolymer, a polyester, or a hydrocarbon-based resin. Other non-limiting polymers include, homopolymers or copolymers of vinyl esters of an aliphatic aid having 1 to 18 carbon atoms, such as vinyl acetate; acrylic acid esters and methacrylic acid esters of an alcohol having 1 to 18 carbon atoms, such as methyl acrylate, ethyl acrylate, butyl acrylate, 2-ethylhexyl acrylate, methyl methacrylate, ethyl methacrylate and butyl methacrylate; and mono and di-ethylenically unsaturated hydrocarbons, including ethylene iso-butylene, styrene and aliphatic dunes, including butadiene, isoprene and chloroprene.

One embodiment of the invention further relates to a composition of the invention which may also comprise an oil phase containing oil soluble or oil dispersible ingredients that are liquid at room temperature (25° C.) and/or oily or waxy substances that are solid at room temperature, such as waxes, semi-solids, gums, and mixtures thereof. This oily phase may also contain organic solvents.

Suitable oily materials that are liquid at room temperature, often referred to as oils, include hydrocarbon-based oils of animal origin such as perhydrosqualene; hydrocarbon-based plant oils such as liquid triglycerides of fatty acids of 4 to 10 carbon atoms, for instance, heptanoic or octanoic acid triglycerides, or oils such as sunflower oil, corn oil, soybean oil, grapeseed oil, castor oil, avocado oil, caprylic/capric acid triglycerides, jojoba oil; linear or branched hydrocarbons of mineral or synthetic origin such as liquid paraffins and derivatives thereof, petroleum jelly; synthetic esters and ethers, in particular esters of fatty alcohols, namely; for example, isopropyl myristate, 2-ethylhexyl palmitate, 2-octyldodecyl stearate, isostearyl isostearate; hydroxylated esters such as isostearyl lactate, octyl hydroxystearate, octyldodecyl hydroxystearate, heptanoates, octanoates and decanoates of fatty alcohols; polyol esters such as propylene glycol dioctanoate, neopentyl glycol diheptanoate, diethylene glycol diisononanoate, and pentaerythritol esters; fatty alcohols containing from 12 to 26 carbon atoms such as octyldodecanol, 2-butyloctanol, 2-hexyldecanol, 2-undecylpentadecanol, oleyl alcohol; partially hydrocarbon-based fluoro oils and/or fluorosilicone oils; silicone oils such as volatile or non-volatile, linear or cyclic polydimethylsiloxanes (PDMS) that are liquid or semisolid at room temperature such as cyclomethicones and dimethicones, optionally comprising a phenyl group, for instance phenyl trimethicones, siloxanes, and mixtures thereof. These oils are usually present in an amount of about 0 weight % to about 90 weight %, preferably from about 1 weight % to about 80 weight % by weight of the oil phase.

The oil phase of the composition of the invention may also comprise one or more cosmetically acceptable organic solvents. These solvents are present in an amount of about 0.1 weight % to about 80 weight %, preferably about 1 weight % to about 50 weight %, based on the total weight of the composition, and may be selected from the group consisting of lipophilic organic solvents, amphiphilic organic solvents and mixtures thereof. Suitable solvents which may be used in the composition of the invention include acetic acid esters such as methyl, ethyl, butyl, amyl or 2-methoxyethyl acetate; isopropyl acetate; hydrocarbons such as toluene, xylene, p-xylene, hexane or heptane; ethers containing at least 3 carbon atoms, and mixtures thereof.

The composition of the invention may further comprise any ingredient conventionally used in the cosmetics field. These ingredients include preserving agents, aqueous phase thickeners (polysaccharide biopolymers, synthetic polymers) and fatty-phase thickeners, fragrances, hydrophilic and lipophilic active agents, and mixtures thereof. The amounts of these various ingredients are those conventionally used in the cosmetics field to achieve their intended purpose, and range typically from about 0.1 weight % to about 20 weight %, based upon the total weight of the composition. The nature of these ingredients and their amounts must be compatible with the production of the compositions of the invention.

The composition of the invention may also comprise an additional particulate phase, typically present in an amount of about 0.1 weight % to about 30 weight %, based upon the total weight of the composition, preferably from about 0.5 weight % to about 20 weight %, and which can comprise pearlescent agents and/or fillers used in cosmetic compositions. Suitable pearlescent agents include mica coated with titanium dioxide or with iron oxide.

Fillers are normally present in an amount of about 0.1 weight % to about 30 weight %, based on the total weight of the composition, preferably about 0.5 weight % to about 15 weight %. Suitable fillers include talc, silica, zinc stearate, mica, kaolin, nylon (in particular orgasol) powder, polyethylene powder, Teflon®, starch, boron nitride, copolymer microspheres such as Expancel® (Nobel Industrie; Sweden), Polytrap® (Dow Corning, Inc.; Midland, Mich.), and silicone resin microbeads (Tospearl®; GE Toshiba Silicones; Japan).

More particularly, the compositions for topical application can be in the form of a protective care composition for the skin, preferably for the face, the neck, the hands, the feet, or other areas of the body. Non-limiting examples include day creams or lotions, night creams or lotions, moisturizer, salves, sunscreen creams, lotions, or oils, ointments, gels, body milks, makeup (a foundation, a bronzer), artificial tanning compositions, depilatories, patches, emulsifiers, or a solid which is poured or cast as a stick or a dish, for example. The inventive compositions are ideal for use in a foundation product because it may achieve high camouflage and blurring effects to result in the perception of a natural appearance.

In another embodiment, the topical compositions of the present invention may also include one or more of the following: a skin penetration enhancer, an emollient, a skin plumper, an optical diffuser, a sunscreen, an exfoliation promoter, and an antioxidant. Details with respect to these and other suitable cosmetic ingredients can be found in the International Cosmetic Ingredient Dictionary (INCI) and Handbook, 10th Edition (2004), published by the Cosmetic, Toiletry, and Fragrance Association (CTFA), at pp. 2177-2299, which is herein incorporated by reference in its entirety.

An emollient provides the functional benefits of enhancing skin smoothness, reducing the appearance of fine lines and coarse wrinkles, and moisturizing. Non-limiting examples include isopropyl myristate, petrolatum, isopropyl lanolate, silicones (e.g., methicone, dimethicone), oils, mineral oils, fatty acid esters, or any mixtures thereof. The emollient is preferably present from about 0.1 weight % to about 50 weight % of the total weight of the composition.

A skin plumper serves as a collagen enhancer to the skin. An example of a suitable, and preferred, skin plumper is palmitoyl oligopeptide. Other skin plumpers are collagen and/or glycosaminoglycan (GAG) enhancing agents. The skin plumper is preferably present from about 0.1 weight % to about 20 weight % of the total weight of the composition.

In addition to the nanoparticles and pigment, optical diffusers or soft focus materials that change the surface optical properties of skin, resulting in a visual blurring and softening of, for example, lines and wrinkles are contemplated. Examples of optical diffusers that can be used in the present invention include, but are not limited to, boron nitride, mica, nylon, polymethylmethacrylate (PMMA), polyurethane powder, sericite, silica, silicone powder, talc, Teflon®, titanium dioxide, zinc oxide, or any mixtures thereof. The optical diffuser is preferably present from about 0.01 weight % to about 20 weight % of the total weight of the composition.

A sunscreen protects the skin from damaging ultraviolet rays. In an illustrative embodiment of the invention, the sunscreen would provide both UVA and UVB protection, by using either a single sunscreen or a combination of sunscreens. Among the sunscreens that can be employed in the present compositions are avobenzone, cinnamic acid derivatives (such as octylmethoxy cinnamate), octyl salicylate, oxybenzone, non-mesoporous titanium dioxide, zinc oxide, or any mixtures thereof. The sunscreen may be present from about 1 weight % to about 30 weight % of the total weight of the composition. The addition of a sunscreen may protect the skin from ultraviolet radiation. As explained above, UV protection may also be achieved by utilizing nanoparticles of about 100 nanometers or less.

The inventive compositions having sunscreen bring about additional improvements to the aesthetic appearance of skin, including at least one of the following: minimizes sunburning, minimizes tanning, and reduces redness.

In an embodiment of the invention, compositions may also have one or more exfoliation promoters. Suitable examples of an exfoliation promoter that can be used in the present compositions include alpha hydroxy acids (AHA); benzoyl peroxide; beta hydroxy acids; keto acids, such as pyruvic acid, 2-oxopropanoic acid, 2-oxobutanoic acid, and 2-oxopentanoic acid; oxa acids as disclosed in U.S. Pat. Nos. 5,847,003 and 5,834,513 (the disclosures of which are incorporated herein by reference); salicylic acid; urea; or any mixtures thereof. One preferred exfoliation promoters are 3,6,9-trioxaundecanedioic acid, glycolic acid, lactic acid, or any mixtures thereof. (See also, INCI at p. 2205).

When an embodiment of the invention includes an exfoliation promoter, the composition has about 0.1 weight % to 30 weight %, preferably about 1 weight % to about 15 weight % and more preferably about 1 weight % to about 10 weight %, of the exfoliation promoter based on the total weight of the composition.

An antioxidant functions, among other things, to scavenge free radicals from skin to protect the skin from environmental aggressors. Examples of antioxidants that may be used in the present compositions include compounds having phenolic hydroxy functions, such as ascorbic acid and its derivatives/esters; beta-carotene; catechins; curcumin; ferulic acid derivatives (e.g. ethyl ferulate, sodium ferulate); gallic acid derivatives (e.g. propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may have an antioxidant preferably from about 0.001 weight % to about 10 weight %, and more preferably from about 0.01 weight % to about 5 weight %, of the total weight of the composition. (See also, INCI at p. 2184).

In one embodiment of the invention, the composition may also have one or more of the following cosmetic and pharmaceutical active agents, excipients, ingredients, or adjuvants: anesthetics, antibiotics, e.g., erythromycins and tetracyclines, salicylic acids, anti-allergenics, antifungals, antiseptics, anti-irritants, anti-inflammatory agents, antimicrobials, analgesics, nitric oxide synthase inhibitors, insect repellents, self-tanning agents, skin penetration enhancers, skin cooling agents, chelating agents, colorants including dyes, lakes and pigments that may be untreated or chemically surface treated to improve wetability or some other property, demulcents, emollients, emulsifiers, fragrances, humectants, lubricants, skin protectants, moisturizers, pH adjusters, preservatives, stabilizers, surfactants, thickeners, plasticizers, viscosity modifiers, vitamins, or any mixtures thereof. The amounts of these various substances are those that are conventionally used in the cosmetic or pharmaceutical fields to achieve their intended purposes, for example, they may constitute from about 0.01% to 20% of the total weight of the composition.

Non-limiting examples of active agents for formulating into the compositions of the invention include those reagents having an effect on the treatment of wrinkles and/or fine lines, in addition to the actives as described, such as keratolytic agents, i.e., an active agent having desquamating, exfoliant, or scrubbing properties, or an active agent which can soften the horny layer of the skin. Other examples of anti-wrinkle or anti-fine line active agents include hydroxy acids and retinoids. These agents can be formulated, for example, in amounts of from about 0.01% to 5% by weight relative to the total weight of the composition.

Suitable hydroxy acids include, for example, glycolic acid, lactic acid, malic acid, tartaric acid, citric acid, 2-hydroxyalkanoic acid, mandelic acid, salicylic acid and alkyl derivatives thereof, including 5-n-octanoylsalicylic acid, 5-n-dodecanoylsalicylic acid, 5-n-decanoylsalicylic acid, 5-n-octylsalicylic acid, 5-n-heptyloxysalicylic acid, 4-n-heptyloxysalicylic acid and 2-hydroxy-3-methylbenzoic acid or alkoxy derivatives thereof, such as 2-hydroxy-3-methyoxybenzoic acid.

Emulsifiers are typically present in the compositions of the invention in an amount of about 0.01 weight % to 30 weight %, by weight and preferably from about 0.1 weight % to 30 weight % by weight relative to the total weight of the composition. However, not all compositions will necessarily include emulsifiers. (See e.g., INCI at p. 2276-2285).

Non-limiting examples of suitable thickening agents include xanthan gum, hydroxypropyl cellulose, hydroxyethyl cellulose, carbomer, gum acacia, Sepigel 305 (available from Seppic Co., France), and clays such as magnesium aluminum silicate. (See, e.g., INCI at p. 2293-2299).

The topical compositions of the present invention may include, and their utility can be enhanced by, one or more humectants, such as ureas, pyrrolidone carboxylic acids, amino acids, sodium hyaluronates, certain polyols and other compounds with hygroscopic properties. (See INCI at p. 2244).

The general activity and mildness to skin of the present topical compositions can also be enhanced by neutralization to pH about 3.5 to about 7.0, most preferably from pH about 3.7 to about 5.6. This neutralization is preferably accomplished with one or more of ammonium hydroxide, potassium hydroxide, sodium hydroxide, arginine or other amino acids, and/or triethanolamine.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

The nanoparticles and pigment of the present invention may be contained in a cosmetically or dermatologically acceptable vehicle, medium, diluent or carrier. The inventive compositions may be further formulated according to procedures known in the art to provide cosmetic compositions such as emulsions, gels, creams, lotions, masks, toners, serums, oils, water-in-oil, oil-in-water, water-oil-water triple emulsions having the appearance of a cream or gel, microemulsions, ointments, pastes, sticks, cakes, pencils, aerosol, and essences, as well as other topical cosmetic vehicles. It is also contemplated that topical compositions of the present invention can be incorporated into delivery systems such as liposomes and topical patches, tapes, and sprays.

In addition, the compositions may be in the form of vesicular dispersions containing ionic and/or nonionic lipids, as described above. Dosage units suitable for such compositions are formulated according to the conventional knowledge and techniques used in the art.

EXAMPLE

The following example describes specific aspects of the invention to illustrate the invention and provide a description of the present methods for those skilled in the art. The example should not be construed as limiting the invention, as the example merely provides specific methodology useful in the understanding and practice of the invention and its various aspects.

This example examines the effect of adding nanoparticles to a composition comprising a color pigment in the concentration enough to effectively create optical effects observed in the moth eye. A Gretag MacBeth Color Eye 7000A Spectrophotometer was used to quantify transmittance, reflection and absorbance (Absorbance=100−(Total Transmittance+SCI Reflection)).

Physical blends of compositions comprising nanoparticles were prepared using a speed mixer with silicone acrylate copolymer (KP 550 from Shin Etsu)—which is 40% polymer in isododecane (IDD). Solutions were cast on clean (optically transparent/colorless) glass plates to give a wet film thickness of approximately 125 microns and dried overnight to form dry films with a resulting dry film thickness of 21-25 microns based on solid content. Samples were prepared in duplicate. Average luminescence (L*) was collected directly using the same sample area for total reflection (specular component included—SCI) and scattered reflection (specular component excluded—SCE). Data was collected in two distinct areas for each sample, resulting in four data points per sample. The Q-test was used to remove erroneous data points. All error bars shown are ± one standard deviation. The summary of prepared samples is shown below in Tables 1 and 2. For the samples reported in Tables 1 and 2, the color pigment is carbon black (D&C Black #2) and values are reported as weight % of the whole composition.

FIG. 2 shows the reflectance (total reflection (SCI) and scattering reflection (SCE)) of compositions 1, 2, 3, and 4 (control) which were prepared as shown in Table 2. The figure shows that the addition of silica nanoparticles of any kind reduces total reflection (SCI—specular component included) without changing diffuse reflection (SCE—specular component excluded), within error limits.

TABLE 2

Physical blends of compositions comprising nanoparticles

| Batch # | Carbon Black, D&C Black #2 | Hydrophobic Silica Shells-SH (Kobo Products) | Cadre Hydrophobic Amorphous Fumed Silica #79684 | Degussa Aeroxide LE 3 Fumed Silica | KP-550, Film former | IDD, Solvent | Total (parts) |
|---|---|---|---|---|---|---|---|
| 1 | 6.94 | 2.78 | 0 | 0 | 6.94 | 83.34 | 100 |
| 2 | 6.94 | 0 | 2.78 | 0 | 6.94 | 83.34 | 100 |
| 3 | 6.94 | 0 | 0 | 2.78 | 6.94 | 83.34 | 100 |
| 4 | 7.14 | 0 | 0 | 0 | 7.14 | 85.72 | 100 |
| 5 | 6.94 | 0 | 0 | 5.00 | 6.94 | 81.12 | 100 |
| 6 | 6.94 | 0 | 0 | 7.00 | 6.94 | 79.12 | 100 |
| 7 | 6.94 | 0 | 5.00 | 0 | 6.94 | 81.12 | 100 |
| 8 | 6.94 | 0 | 7.00 | 0 | 6.94 | 79.12 | 100 |
| 9 | 9.00 | 0 | 0 | 2.78 | 6.94 | 81.28 | 100 |
| 10 | 11.0 | 0 | 0 | 2.78 | 6.94 | 79.28 | 100 |
| 11 | 9.00 | 0 | 0 | 5.00 | 6.94 | 79.06 | 100 |
| 12 | 0 | 0 | 7.14 | 0 | 7.14 | 85.72 | 100 |
| 13 | 0 | 0 | 0 | 7.14 | 7.14 | 85.72 | 100 |

Figure 3:
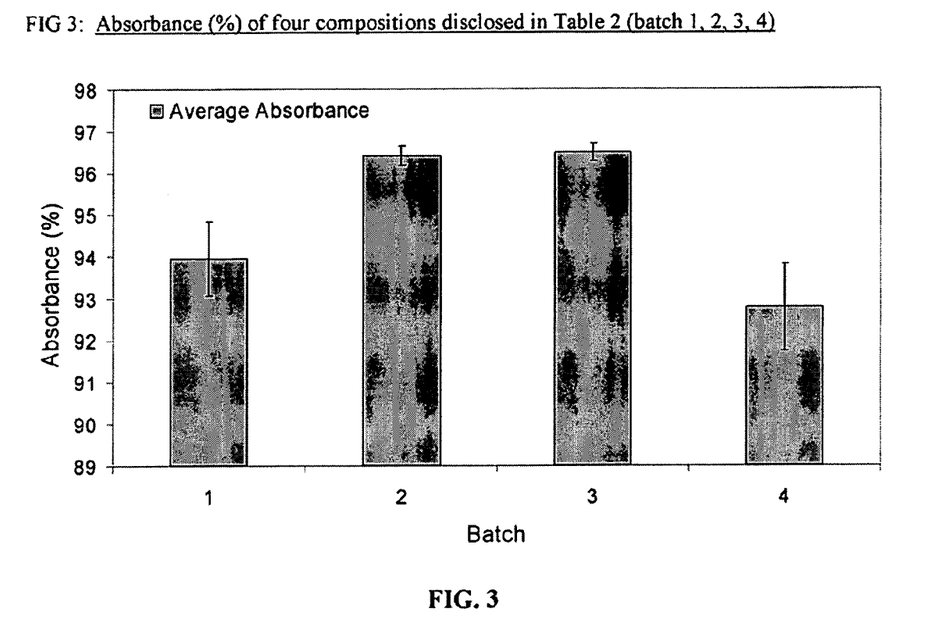

FIG. 3 shows the absorbance of compositions 1, 2, 3, and 4 (control) which were prepared as shown in Table 2. The figure shows that the addition of silica of any kind increases absorption as compared to a pigment alone (composition 4).

FIG. 4 shows the reflectance (total reflection (SCI) and scattering reflection (SCE)) of compositions 5, 6, 9, 11, and 4 (control) which were prepared as shown in Table 2. The figure shows that the addition of fumed silica to carbon black causes a decrease in total reflection and scattered reflection.

FIG. 5 shows the absorbance of compositions 5, 6, 9, 11, and 4 (control) which were prepared as shown in Table 2. The figure shows that the addition of fumed silica to carbon black causes a decrease in total reflection.

Table 3 summarizes the reflectance and absorbance of all compositions which were prepared as shown in Table 2.

TABLE 3

Absorbance and total reflectance of compositions disclosed in Table 2

| Batch | Average L* (ref-SCI) | STDEV L* (ref-SCI) | Average L* (ref-SCE) | STDEV L* (ref-SCE) | Absorbance | STD Dev (Abs) |
|---|---|---|---|---|---|---|
| 1 | 20.50 | 0.69 | 20.26 | 0.62 | 93.95 | 0.89 |
| 2 | 21.88 | 0.92 | 16.91 | 1.14 | 96.41 | 0.24 |
| 3 | 21.80 | 0.82 | 16.94 | 1.02 | 96.49 | 0.21 |
| 4 | 31.94 | 0.08 | 18.68 | 4.47 | 92.79 | 1.04 |
| 5 | 20.30 | 0.88 | 14.87 | 0.19 | 96.63 | 0.20 |
| 6 | 17.92 | 0.49 | 14.19 | 0.44 | 96.01 | 1.13 |
| 7 | 16.98 | 0.28 | 14.37 | 0.47 | 96.77 | 0.50 |
| 8 | 16.11 | 0.22 | 14.97 | 0.03 | 95.05 | 1.00 |
| 9 | 22.65 | 1.11 | 17.72 | 1.53 | 96.06 | 0.34 |
| 10 | 20.53 | 0.81 | 16.49 | 0.77 | 96.80 | 0.16 |
| 11 | 19.89 | 1.37 | 15.37 | 0.69 | 95.51 | 1.55 |
| 12 | 56.63 | 4.51 | 54.11 | 5.64 | 3.37 | 5.88 |
| 13 | 66.24 | 2.64 | 65.84 | 2.67 | 7.17 | 4.49 |

FIGS. 2-5 show that while the efficiency of color chroma and reduction of glossiness is dependent on the nanoparticle loading (wt %) and is effective for the types of silica tested, the greatest increase in absorbance was obtained when the silica (nanoparticle) to carbon-black (pigment) ratio is approximately 1.0:1.4.

Table 4 lists properties of three batches of compositions of this invention with fumed silica (Degussa Aeroxide LE 3, fumed silica) nanoparticles along with a control batch without any nanoparticles (the full compositions of which are disclosed in Table 2). Table 4 shows that the presence of nanoparticles in a composition enhances the absorbance. In addition, Table 4 shows that as the weight ratio of nanoparticles plus pigment to film former increases, the percent total reflectance decreases.

TABLE 4

Absorbance and reflectance of compositions with and without fumed silica (Aeroxide LE 3) nanoparticles.

| Batch# | Weight % carbon black (pigment) | Weight % Aeroxide LE 3 (nanoparticles) | Weight % KP-550 (film former) | Weight ratio of pigment plus nanoparticles to film former | % Absorbance | Total Reflectance |
|---|---|---|---|---|---|---|
| 4 (Control) | 7.14 | 0 | 7.14 | 10:1.0 | 92.8 | 7.0 |
| 3 | 6.94 | 2.78 | 6.94 | 1.4:1.0 | 96.5 | 3.5 |
| 5 | 6.94 | 5.00 | 6.94 | 1.7:1.0 | 96.6 | 3.1 |
| 6 | 6.94 | 7.00 | 6.94 | 2.0:1.0 | 96.0 | 2.5 |

FIG. 6a shows the absorbance for three (3) systems: 4.00% carbon black control with no nanoparticles (batch 14), 4.00% carbon black with 4.00% silica shell nanoparticles (batch 15), and 4.00% carbon black with 4.00% fumed silica nanoparticles (batch 16) which were prepared as shown in Table 5. FIG. 6b shows the luminescence (L*) data for the three systems in FIG. 6a. The figures shows that the addition of either 4.00% fumed silica nanoparticles or 4.00% silica shell nanoparticles results in increased absorbance and reduced luminescence resulting in enhanced contrast (darker) in comparison to the carbon black control no nanoparticles).

TABLE 5

Physical blends of compositions comprising nanoparticles

| Batch # | Carbon Black, D&C Black #2 | Hydrophobic Silica Shells-SH (Kobo Products) | Degussa Aeroxide LE 3 Fumed Silica | KP-550, Film former | IDD, Solvent | Total (parts) |
|---|---|---|---|---|---|---|
| 14 | 4.00 | 0 | 0 | 7.00 | 89.00 | 100 |
| 15 | 4.00 | 4.00 | 0 | 7.00 | 85.00 | 100 |
| 16 | 4.00 | 0 | 4.00 | 7.00 | 85.00 | 100 |

Table 6 summarizes the reflectance and absorbance of all compositions which were prepared as shown in Table 5.

TABLE 6

Absorbance and total reflectance of compositions disclosed in Table 5

| Batch | Average L* (ref-SCI) | Average L* (ref-SCE) | Average Absorbance | Transmission | Total L* (SCI) |
|---|---|---|---|---|---|
| 14 | 29.91 | 3.28 | 93.73 | 0.08 | 6.2 |
| 15 | 27.04 | 5.03 | 94.86 | 0.03 | 5.1 |
| 16 | 21.32 | 2.98 | 95.15 | 1.51 | 3.3 |

FIG. 7a shows the total transmission for three (3) systems: 4.00% carbon black control with no nanoparticles (batch 14), 4.00% carbon black with 4.00% silica shell nanoparticles (batch 15), and 4.00% carbon black with 4.00% fumed silica nanoparticles (batch 16). FIG. 7b shows the total reflectance and scattered reflectance data for the three systems in FIG. 7a. The figures show that addition of 4.00% fumed silica nanoparticles results in increased transmission, reduced total reflectance and reduced scattered reflectance.

The content of all patents, patent applications, published articles, abstracts, books, reference manuals and abstracts, as cited herein are hereby incorporated by reference in their entireties to more fully describe the state of the art to which the invention pertains. All concentrations recited in the specification and claims are reported as weight percents, unless otherwise indicated.

It should be understood that the foregoing description is only illustrative of the present invention. Various alternatives and modifications can be devised by those skilled in the art without departing from the invention. Accordingly, the present invention is intended to embrace all such alternatives, modifications and variations that fall within the scope of the appended claims.

What is claimed is:

1. A method of reducing light reflection from a biological surface by applying to said biological surface a layer of a composition comprising:
   (a) a plurality of hydrophobic fumed silica nanoparticles, the fumed silica nanoparticles having a particle size less than the wavelength of visible light;
   (b) a combination of iron oxide and carbon black pigments; and
   (c) a cosmetically or pharmaceutically acceptable carrier comprising one or more of a film former or wax;
   wherein the weight ratio of hydrophobic fumed silica nanoparticles to pigment is between about 1.0:1.0 and about 1.0:10.0; and wherein said layer of said composition provides a dry film having an L* value of 25 or less.

2. The method of claim 1, wherein mean particle size of the iron oxide pigment is in the range of from about 100 nm to about 2 microns.

3. The method of claim 1, wherein the hydrophobic fumed silica nanoparticles range in size from about 10 nm to about 500 nm.

4. The method of claim 1, wherein the hydrophobic fumed silica nanoparticles range in size from about 100 nm to about 300 nm.

5. The method of claim 1, wherein the mean particle size of the hydrophobic fumed silica nanoparticles is about 200 nm.

6. The method of claim 1, wherein the weight ratio of silica to pigment is about 1:0 to about 1:3.

7. The method of claim 1, wherein the film former is selected from the group consisting of sulfopolyester resins, polyvinylacetate, polyvinyl alcohol polymers, acrylic resins, silicone acrylate polymers, polyvinylpyrrolidones, high molecular weight silicones, organosiloxanes, polyurethanes, and hydrophobic acrylate copolymers or a mixture thereof.

8. The method of claim 1, wherein the film former is silicone acrylate copolymer.

\* \* \* \* \*